United States Patent
Salter, Jr.

(10) Patent No.: US 6,634,790 B1
(45) Date of Patent: Oct. 21, 2003

(54) TOMOTHERAPY TREATMENT TABLE POSITIONING DEVICE

(75) Inventor: Bill J. Salter, Jr., Boerne, TX (US)

(73) Assignee: The University of Texas System, Austin, TX (US)

( * ) Notice: Subject to any disclaimer, the term of this patent is extended or adjusted under 35 U.S.C. 154(b) by 61 days.

This patent is subject to a terminal disclaimer.

(21) Appl. No.: 09/624,058

(22) Filed: Jul. 24, 2000

Related U.S. Application Data

(63) Continuation of application No. 09/176,716, filed on Oct. 21, 1998, now Pat. No. 6,152,599.

(51) Int. Cl.$^7$ .............................................. A61B 6/04
(52) U.S. Cl. ..................... 378/209; 378/68; 378/177; 378/195; 5/601
(58) Field of Search ................. 378/193, 195, 378/209, 204, 205, 68, 177, 65; 5/601

(56) References Cited

U.S. PATENT DOCUMENTS

| | | | |
|---|---|---|---|
| 3,240,935 A | 3/1966 | Dougall | .................. 5/601 |
| 3,424,470 A | 1/1969 | Voster | |
| 3,588,500 A | 6/1971 | Koerner | |
| 3,783,251 A | 1/1974 | Pakovich | .................. 378/65 |
| 3,840,221 A | 10/1974 | Hogan | |
| 4,230,129 A | 10/1980 | LeVeen | |
| 4,409,860 A | 10/1983 | Moriyama et al. | |
| 4,552,347 A | 11/1985 | Wallis | |
| 4,718,077 A | 1/1988 | Moore et al. | |
| 4,885,998 A | 12/1989 | Span et al. | |
| 5,014,292 A | 5/1991 | Siczek et al. | |
| 5,090,401 A | 2/1992 | Schwieker | .................. 378/205 |
| 5,155,758 A | 10/1992 | Vogl | |
| 5,239,716 A | 8/1993 | Fisk | |
| 5,475,885 A | 12/1995 | Ishikawa | .................. 5/601 |
| 5,596,779 A | 1/1997 | Meek | |
| 5,727,042 A | 3/1998 | Brenneisen | |
| 5,808,468 A * | 9/1998 | Bis et al. | .................. 5/601 |
| 6,152,599 A * | 11/2000 | Salters, Jr. | .................. 378/209 |
| 6,240,582 B1 * | 6/2001 | Reinke | .................. 5/601 |
| 6,269,499 B1 * | 8/2001 | Amir | .................. 5/601 |
| 6,416,219 B1 * | 7/2002 | Pflaum et al. | .................. 378/209 |
| 6,499,159 B1 * | 12/2002 | Schmitt et al. | .................. 5/601 |
| 2002/0120986 A1 * | 9/2002 | Erbel et al. | .................. 5/601 |

FOREIGN PATENT DOCUMENTS

WO    WO 98/04194    2/1998

OTHER PUBLICATIONS

Novalis; Shaped–Beam Stereoactic Radiosurgery Press Release; Apr. 11, 1997.
Novalis; Radiosurgery System brochure; undated.

\* cited by examiner

*Primary Examiner*—Drew A. Dunn
(74) *Attorney, Agent, or Firm*—Rosenthal & Osha L.L.P.

(57) ABSTRACT

An integrated positioning device for a tomotherapy treatment couch is disclosed. The integrated positioning device has a central frame, two positioning tables, and an attachment arm. The central frame is mounted on the base of the tomotherapy treatment couch. The positioning tables position the moveable tabletop of the treatment couch in the lateral and longitudinal directions. Each table is able to position and lock the tabletop in one of the directions to a high degree of accuracy. The attachment arm connects the positioning tables to the tabletop and holds the tabletop in position for tomotherapy treatments.

37 Claims, 9 Drawing Sheets

TOMOTHERAPY TREATMENT TABLE POSITIONING DEVICE

This application is a continuation of U.S. application Ser. No. 09/176,716, filed on Oct. 21, 1998 now U.S. Pat. No. 6,152,599.

FIELD OF INVENTION

The invention relates to tomotherapy treatment and more particularly to an apparatus and method for precisely positioning a tomotherapy treatment table.

BACKGROUND

Intensity modulated radiation therapy (IMRT) is an emerging technique in the treatment of tumors. It involves the delivery of many small, concentrated "pencil beams" of radiation that can be varied in intensity. The primary goal of tomotherapy is to deliver a very high dose of radiation to the tumor, while sparing the surrounding tissue. In order to spare the surrounding tissue, this technique causes the high dose of radiation to conform to the shape of the tumor. Tomotherapy delivers a treatment to the tumor in a slice by slice procedure. One thin slice of the tumor is treated at a time before moving on to treat the next slice. The three dimensional shape of the tumor is programmed into a computer which controls the treatment. Because of the high doses of radiation involved and the desirability of having the high dose region essentially the exact size and shape of the tumor, extreme accuracy in positioning the patient is required. The necessary accuracy is maintained by aligning the linear accelerator's isocenter to a precise point within the patient. The isocenter is a single reference point in the x-y-z plane which serves to orient the radiation beams to the proper coordinates of the slices of the tumor.

FIG. 1 shows an example of equipment for performing such a technique. A linear accelerator 10 provides the radiation for the therapy. A multi-leaf collimator 14 concentrates the radiation into the pencil beams which are applied to the tumor. Each pencil beam is approximately one square centimeter in size. The multi-leaf collimator 14 is mounted on the head 13 of the linear accelerator 10 which rotates on a gantry 12 around the patient. The patient is immobilized on a treatment couch 16 which comprises a tabletop 18, a positioning rail 20, and a base 22. The tabletop 18 is able to move independently of the base 22 in the lateral (x-axis) and/or longitudinal (y-axis) directions. The base 22 is moveable in the vertical directions (z-axis). This allows the patient, who is lying on the tabletop, to be positioned to the desired x, y, z location.

It is often advantageous to rotate the treatment couch 16 to a different angle (called a "couch angle") with respect to the linear accelerator 10 in order to treat the tumor from a different direction (i.e., on a different plane). The entire couch assembly may be rotated about the isocenter line of the collimator 15, because it is attached to a rotating disc assembly 24 mounted in the floor. The couch 16 is attached to the edge of the rotational disc 24 such that when the disc 24 is rotated, the couch angle is adjusted accordingly.

Research has shown that there are advantages to delivering IMRT treatments when the isocenter of the linear accelerator is intentionally placed somewhere other than the center of the tumor. For such "non-isocentric" delivery schemes, when the couch angle is changed, basic trigonometry dictates that the treatment couch must make lateral and longitudinal translations to maintain the original isocenter at the same point within the patient. These translations must be done With sub-millimeter accuracy relative to the isocenter. One prior art method performs these translations using a self-supporting positioning device known as the "Crane™" which is available from the Nomos Corporation as part of its Peacock System® radiosurgery device. FIG. 2 shows a side view of the prior art positioning device. FIG. 3 shows the overhead view of the same device. The positioning device 26 comprises a central vertical beam 28 which is supported by three legs 30. The device 26 is moved by retractable wheels 32 which are recessed within the legs 30 when the device is stationary. The central beam 28 supports a lateral positioning arm 34 which extends through a lateral arm housing 35. The location of the lateral positioning arm 34 is adjusted by a lateral movement crank 36. The lateral positioning arm 34 is connected to the longitudinal arm housing 39. A longitudinal positioning arm 38 extends through the longitudinal housing 39. The location of the longitudinal arm 38 is controlled by a longitudinal movement crank 40. Two attachment arms 42 are mounted on top of the longitudinal arm housing 39. These arms 42 attach to the positioning rail 20 of the tabletop 18 (shown in FIG. 1) with attachment clamps 44 which are tightened with attachment cranks 46.

A device of the type shown in FIGS. 2 and 3 is, by design, very heavy (approximately 300 lbs.). When the couch angle is changed, the positioning device is elevated onto its wheels and dragged or pulled alongside the treatment couch as it rotates to the new angle. When the device is elevated onto the wheels, however, it exerts compressive, tensile, and/or shear forces on the attachment arms. These forces alter the position of the treatment couch relative to the device and, consequently, invalidate any previously set isocenter. Additional large forces also are exerted on the attachment arms when the device is dragged or pushed by the treatment couch while it is moving. These forces alter the position of the couch in relation to the device. Furthermore, the length of the lateral and vertical positioning alms, which is necessitated by the free standing design, makes the device prone to "flexing" of the system, which can induce clinically significant errors. In combination, these forces can, individually and collectively, result in significant errors of as much as 1 cm or more. Therefore, in practice, accurate treatment at multiple couch angles utilizing non-isocentric IMRT delivery schemes are currently not practical.

SUMMARY OF INVENTION

The invention relates to a tomotherapy treatment table positioning device for positioning the tabletop with a high degree of accuracy.

In general, in one embodiment, the invention relates to an apparatus for positioning a moveable tabletop on a treatment couch comprising: a central frame which is mounted to the treatment couch; a connecting mechanism attached to the moveable tabletop, the connecting mechanism extending from the central frame; and a positioning mechanism on the central frame which positions the moveable tabletop to a desired location in lateral and longitudinal directions.

In another embodiment, the invention relates to an apparatus for positioning a moveable tabletop on a treatment couch comprising: means for mounting a central frame to the base of the treatment couch; means for connecting the central frame to the moveable tabletop; means for positioning the moveable tabletop to a desired location in a lateral direction; and means for positioning the moveable tabletop to a desired location in a longitudinal direction.

In another embodiment, the invention relates to a method for positioning a moveable tabletop on a treatment couch to receive radiation treatment comprising: providing a central frame mounted on the treatment couch; attaching at least one connecting mechanism to the moveable tabletop, the connecting mechanism(s) extending from the central frame; and positioning the moveable tabletop to a desired location in lateral and longitudinal directions.

The advantages of the invention include, at least, an integrated positioning device that is mounted on the treatment couch. Another advantage is the capability of the device to position and lock the tabletop of the couch in the lateral and longitudinal positions to an accuracy of less than 0.01 mm. When the treatment couch is rotated to a different couch angle, the integrated positioning device rotates as an integral part of the couch and as a result, it maintains the positioning accuracy of the tabletop relative to the isocenter of the patient.

DETAILED DESCRIPTION

Figure 1:
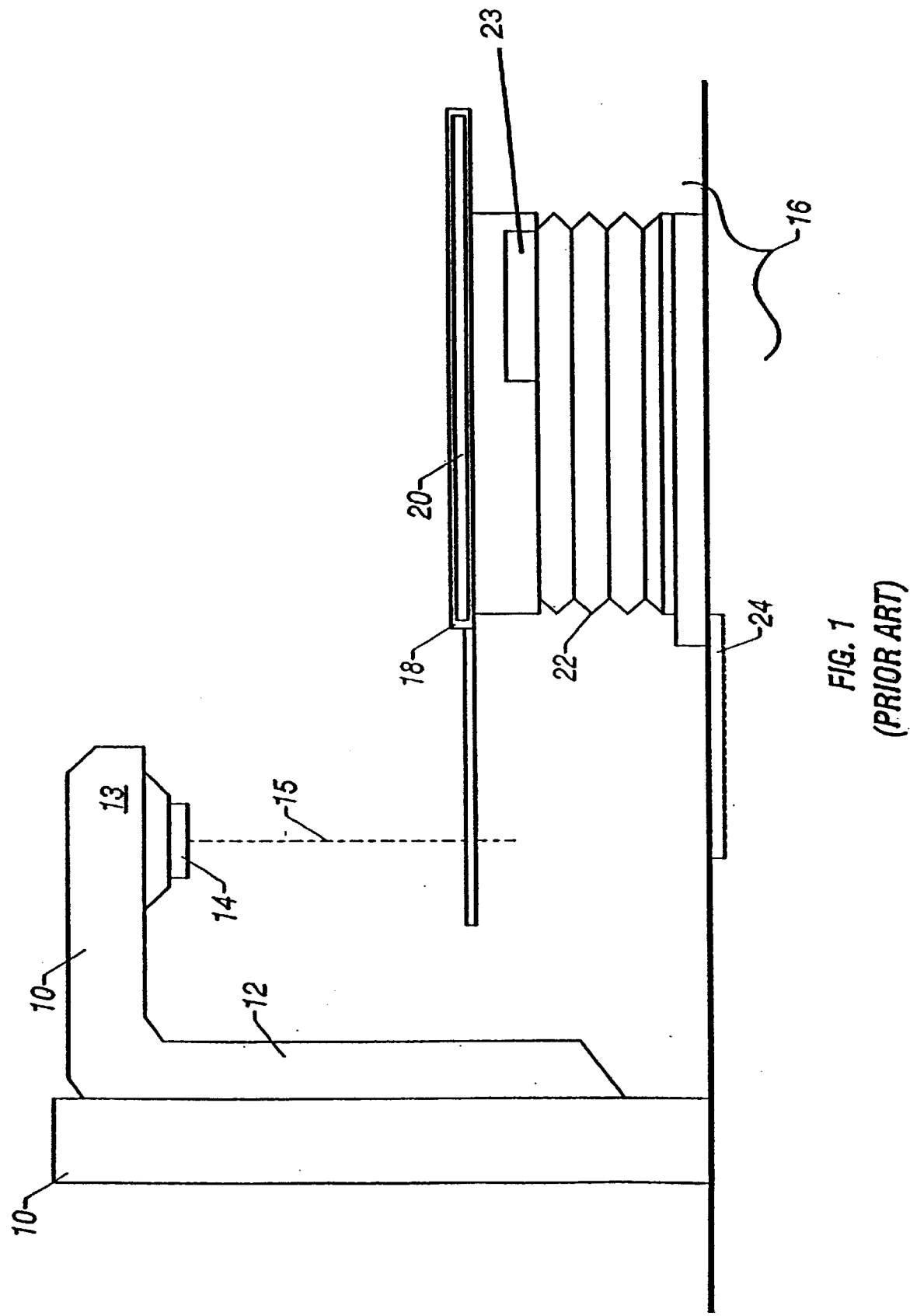
FIG. 1 is a side view of a conventional radiation treatment apparatus with a linear accelerator and a rotating treatment couch.
Figure 2:
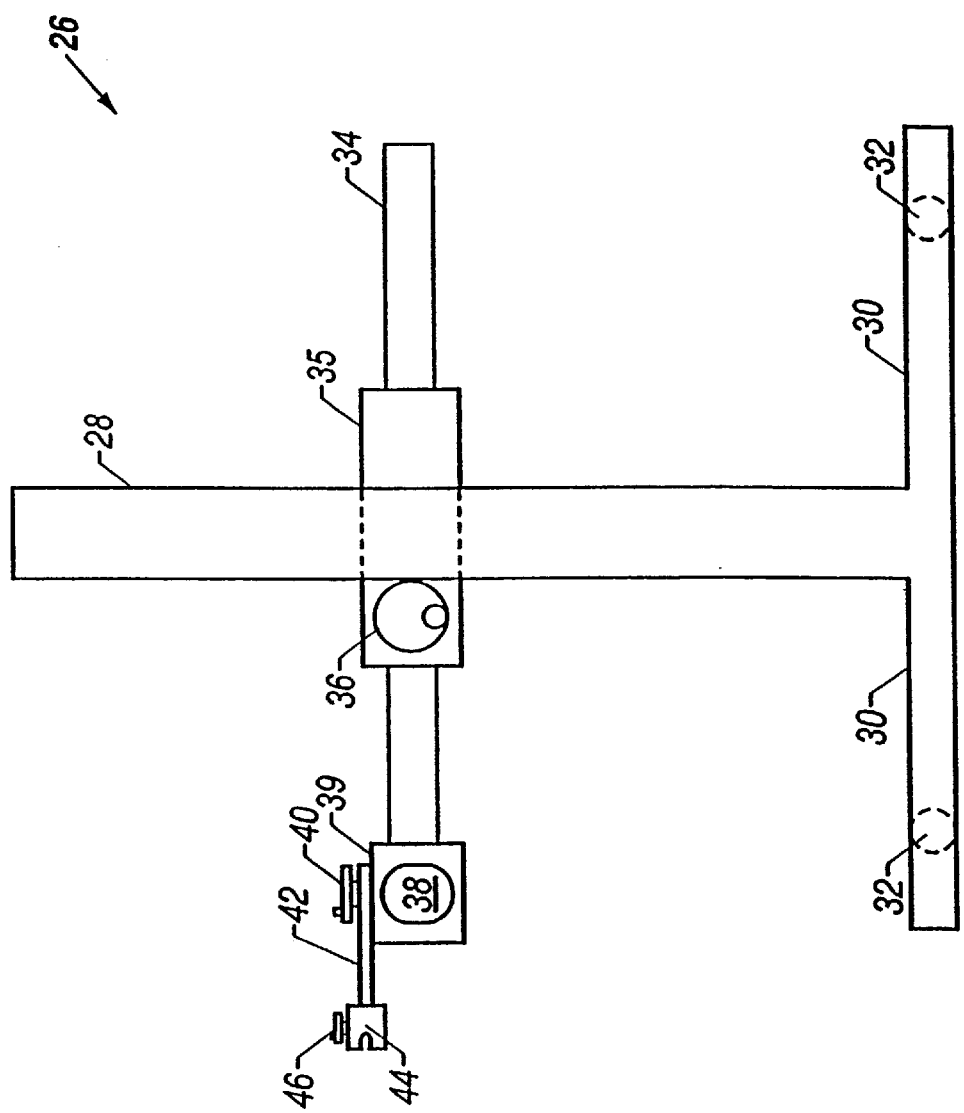
FIG. 2 is a side view of a prior art positioning device for a treatment couch tabletop.
Figure 3:
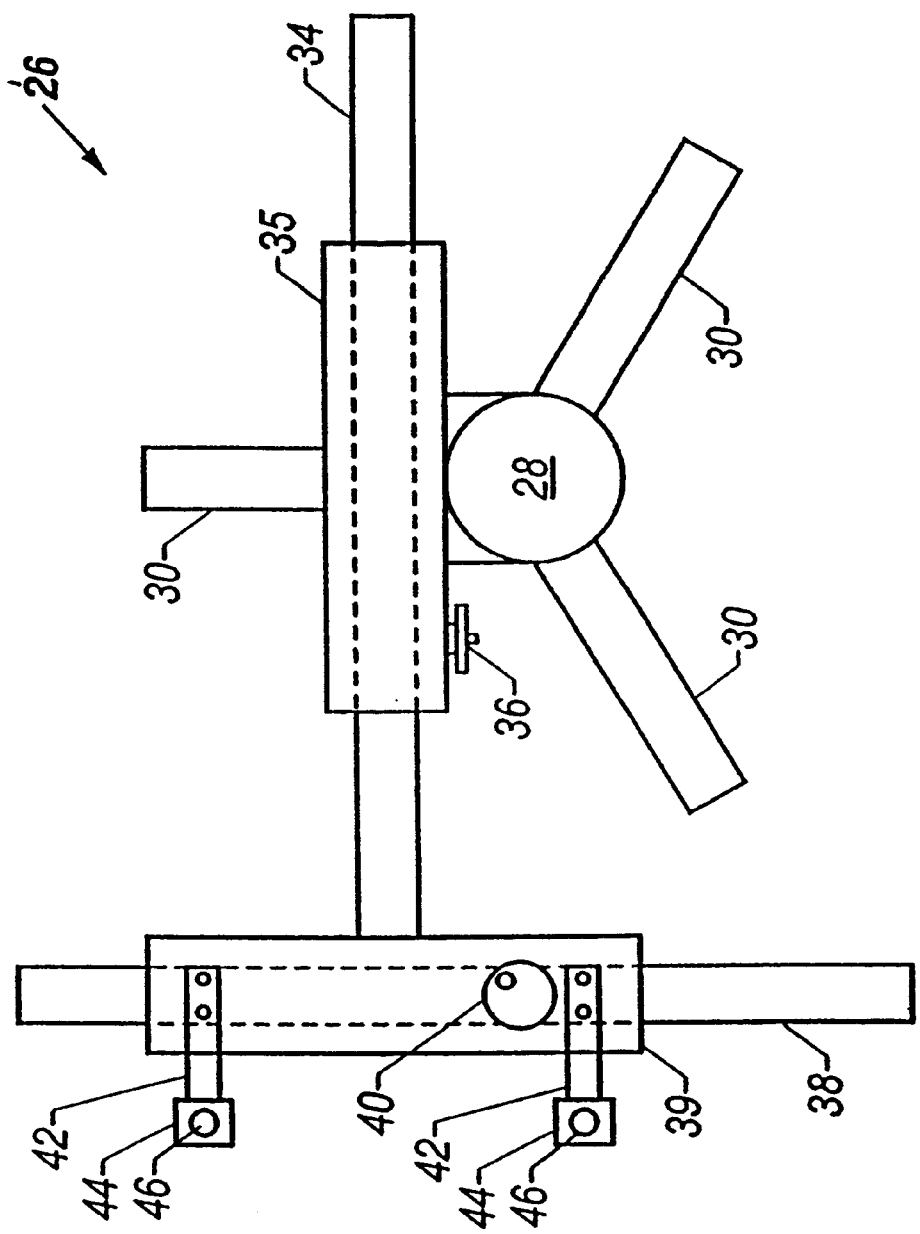
FIG. 3 is an overhead view of the device of FIG. 2.

Exemplary embodiments of the invention will be described with reference to the accompanying drawings. Like items in the drawings are shown with the same reference numbers.

Figure 4:
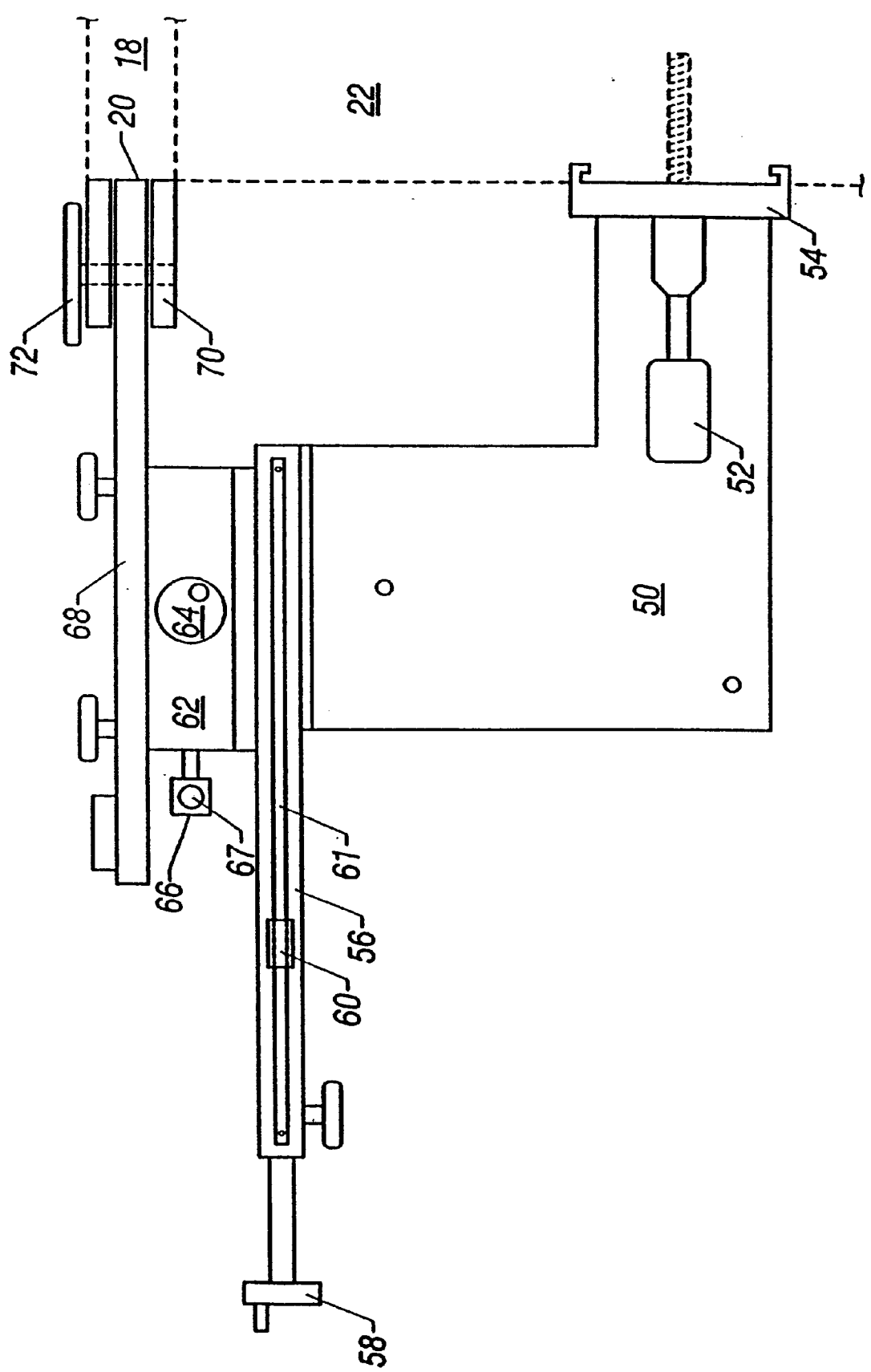
FIG. 4 is a side view of an integrated positioning apparatus for a treatment couch tabletop in accordance with an embodiment of the invention.
Figure 5:
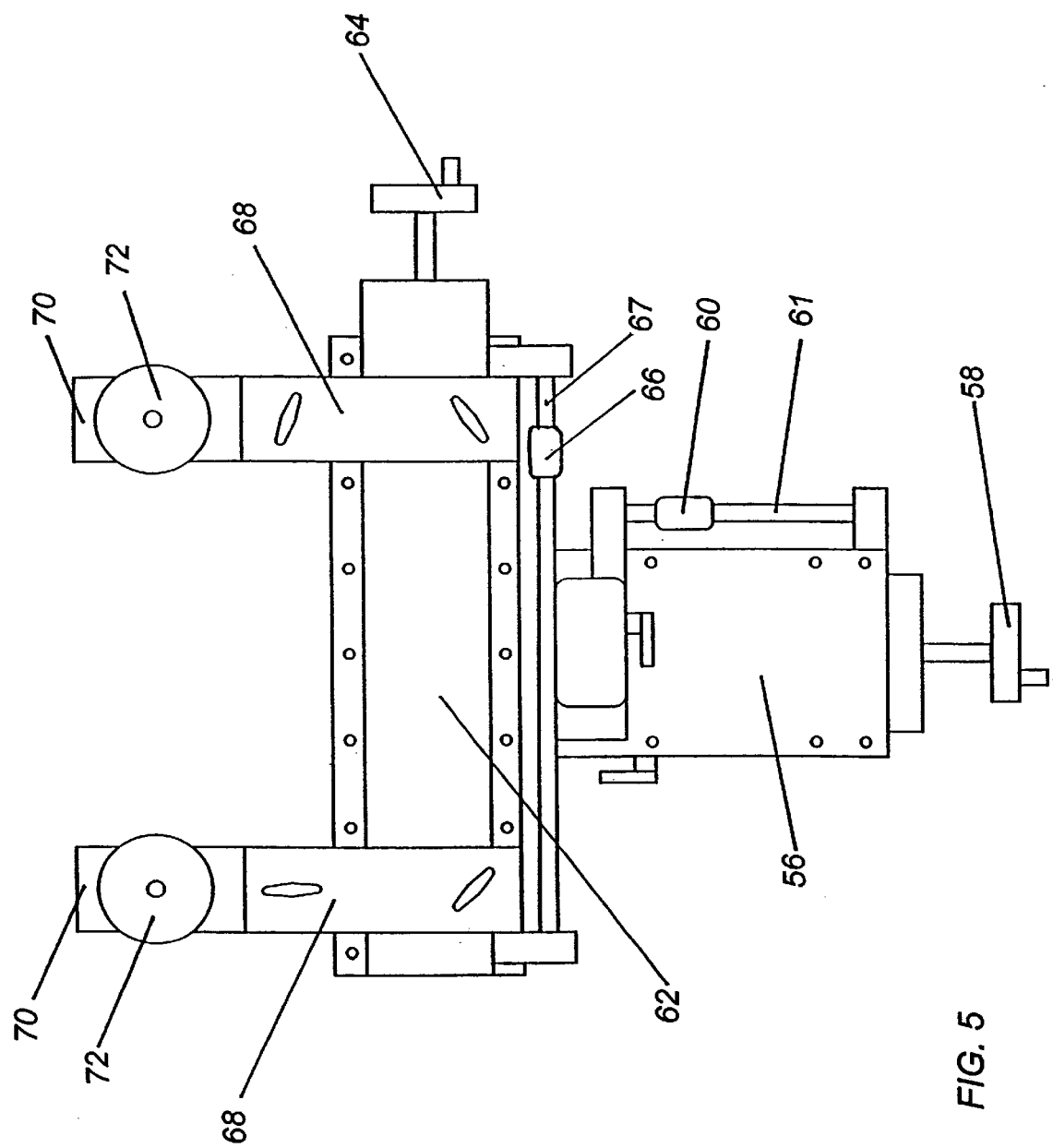
FIG. 5 is an overhead view the embodiment of FIG. 4.

FIG. 4 shows a side view of one embodiment of a tabletop positioning device which is integrated with the treatment couch 16. FIG. 5 shows the overhead view of the same embodiment. In this embodiment, the integrated positioning device comprises a mounting frame (central frame) 50 which is mounted on an exterior of the base 22 of the treatment couch, a lateral positioning table 56, a longitudinal positioning table 62, and two attachment arms 68.

The mounting frame 50 has a perpendicular mounting plate 54 which attaches to a similar couch plate 23, which is shown in FIG. 1, that is permanently mounted to the couch base. A mounting bolt 52 extends through the mounting plate 54 and into the couch plate 23 to secure the frame to the treatment couch. Another mounting bolt (not shown) also extends through the mounting plate 54 and into the couch plate 23 on the opposite side of the mounting frame 50. In some embodiments, the mounting bolts 52 are spring loaded capture screws. These capture screws have large knurled hand knobs for easy and quick installation and removal. The capture screws are mounted into predrilled alignment holes in the couch plate 23 of the treatment couch. While two bolts may be used in some embodiments, any alternative methods, including any type of temporary or permanent attachment means, could be used in other embodiments to adequately secure the mounting frame 50 to the base 22.

The lateral positioning table 56 controls the lateral (x-axis) movement of the tabletop 18. The lateral positioning table 56 is adjusted by an end mounted lateral movement crank 58. A lateral position indicator 60 is mounted on a rail 61 to provide a digital readout of the exact lateral position (e.g., ±0.01 mm) of the table 56. The longitudinal positioning table 62 is attached to the lateral positioning table 56. The longitudinal table 62 controls the longitudinal (y-axis) movement of the tabletop 18. An end mounted longitudinal movement crank 64.is used to adjust the table 62. A longitudinal position indicator 66 is mounted on a rail 67 to provide a digital readout of the exact longitudinal position (e.g., ±0.01 mm) of the longitudinal table 62. In alternative embodiments, both positions can he displayed with an analog means such as a calibrated ruler or a marked scale.

The attachment arms 68 are mounted on top of the longitudinal positioning table 62. The arms 68 are attached to the positioning rail 20 of the tabletop 18 of the treatment couch. The arms 68 attach to the rail 20 with attachment clamps 70 which are tightened by cranks 72. While two arms are shown in this embodiment, one attachment arm or multiple attachment arms may be used to adequately attach the device to the tabletop. Further, alternative embodiments may use different types of connecting mechanisms to secure the device to the tabletop of the treatment couch.

The positioner tables may be machinist-type positioning tables. Their movement is controlled with hand cranks which use pre-loaded bearings. In one embodiment, one revolution of the crank results in movement of 1 millimeter by the table. The position of the tables are determined by optical readout devices (not shown) that are designed to read encoded gradations on a bar attached to the geared shafts of the crank. These readings are then reported as a numerical position of the shaft to the position indicators on the positioning tables. These positioning indicators may be battery powered electronic readout devices that are commonly available equipment used for positioning cameras or telescopes.

When constructed as described above, the tables have an accuracy of 0.01 mm. This high degree of accuracy is possible because the tables have minimal gear slop due to the positioning tables' use of pre-loaded bearings. Gear slop, also referred to as historesis, is an incorrect indication of position due to changes in the direction of motion of the positioner tables. Although some embodiments may be capable of locking the tabletop position to prevent unwanted movement in both the lateral and longitudinal directions, this has been observed to be unnecessary in normal clinical implementation because of minimal gear slop.

Figure 6:
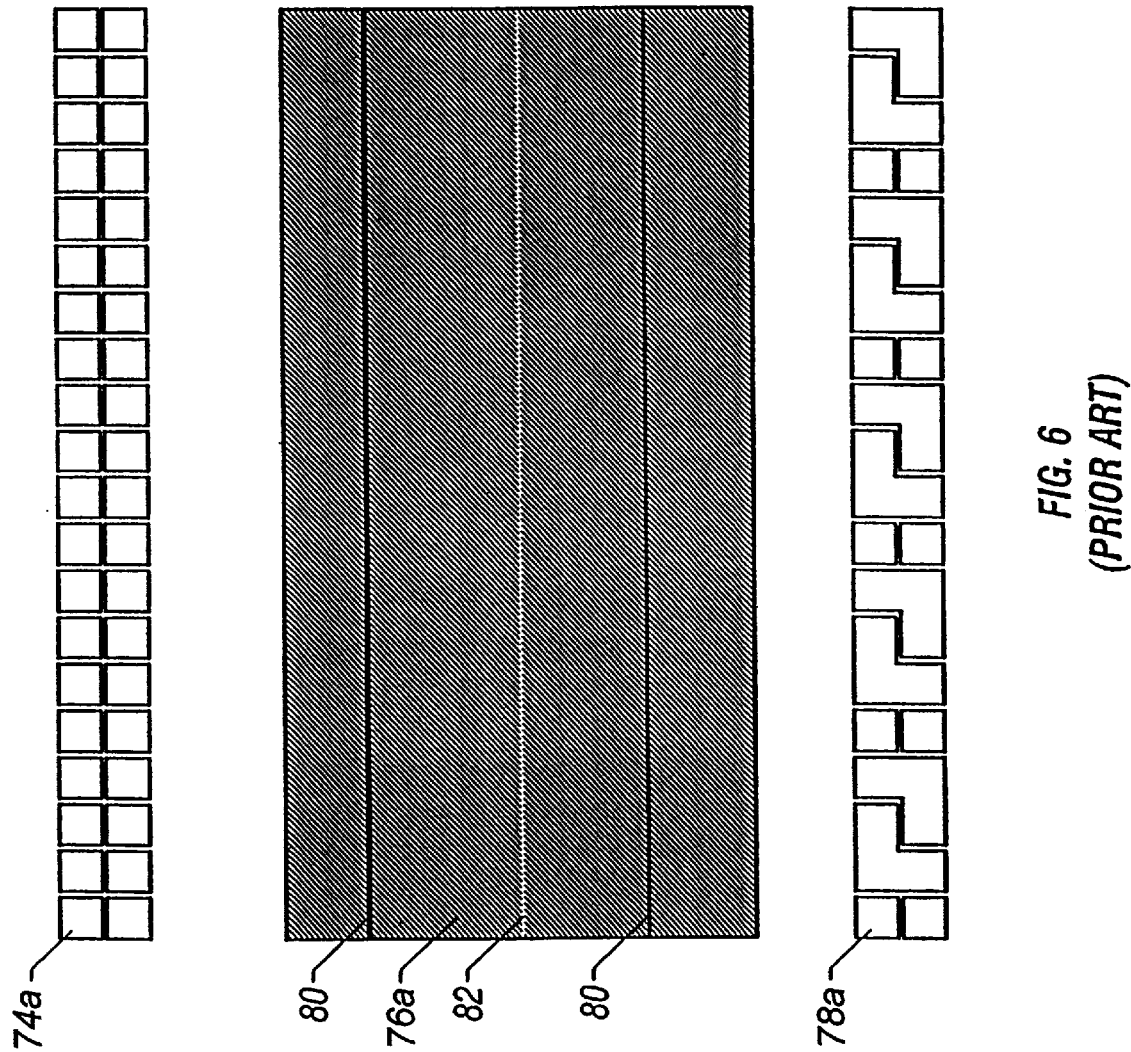
FIG. 6 illustrates the results of accuracy tests which were made using a prior art positioning device.
Figure 7:
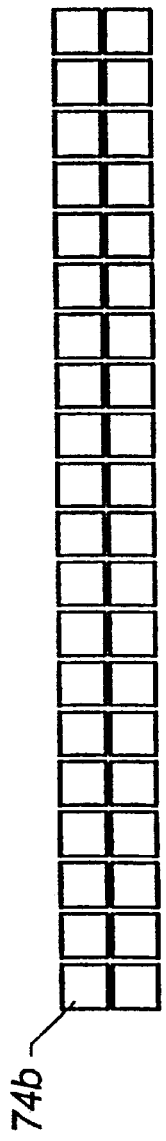
FIG. 7 illustrates the results of accuracy tests which were made using an integrated positioning apparatus in accordance with an embodiment of the invention.
Figure 7:
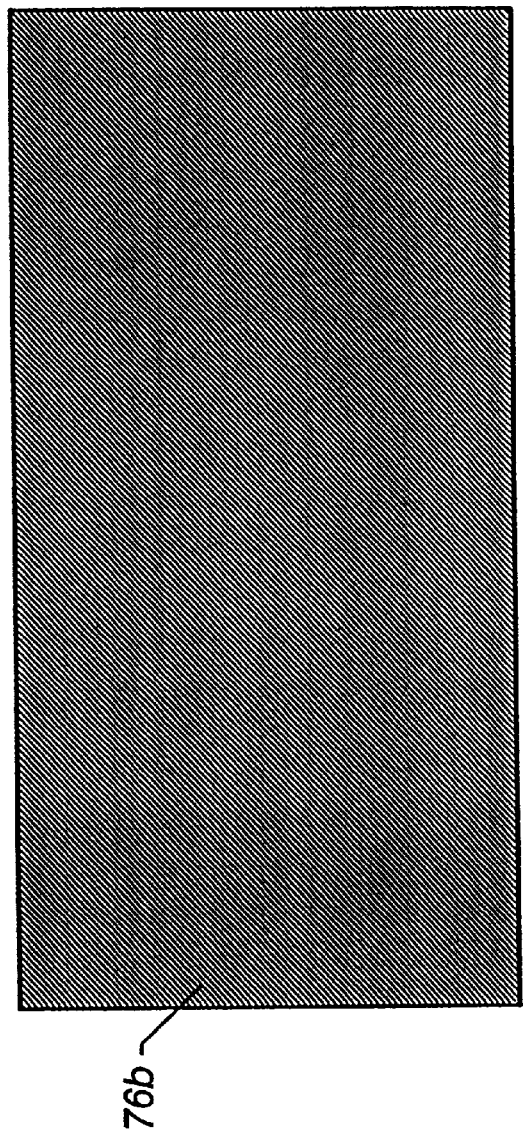
Figure 7:
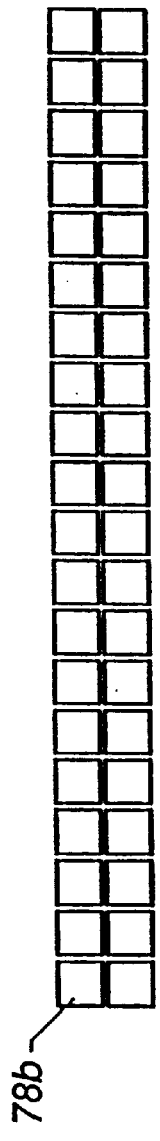
Figure 8:
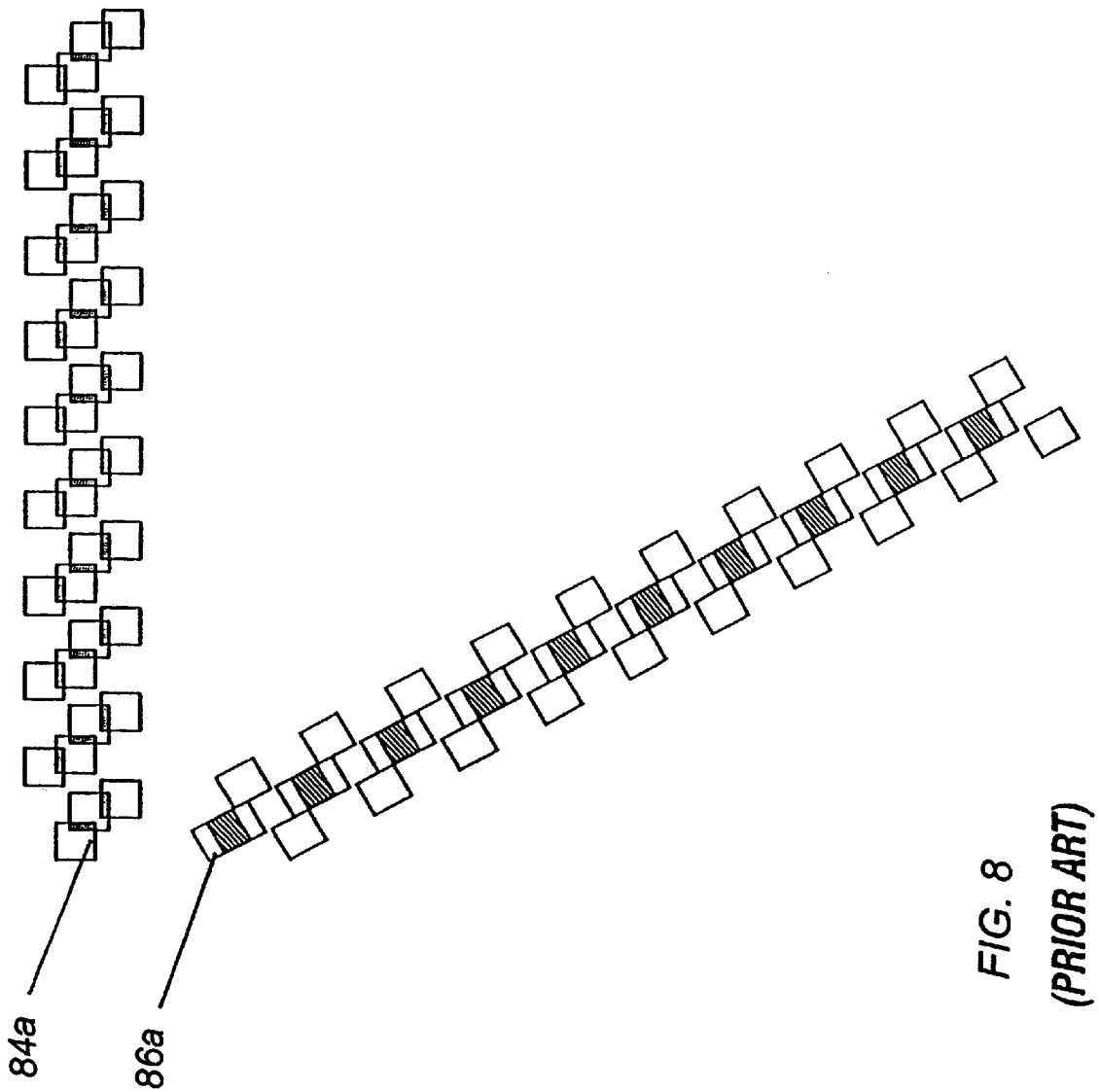
FIG. 8 illustrates the results of rotational accuracy tests which were made using a prior art positioning device.
Figure 9:
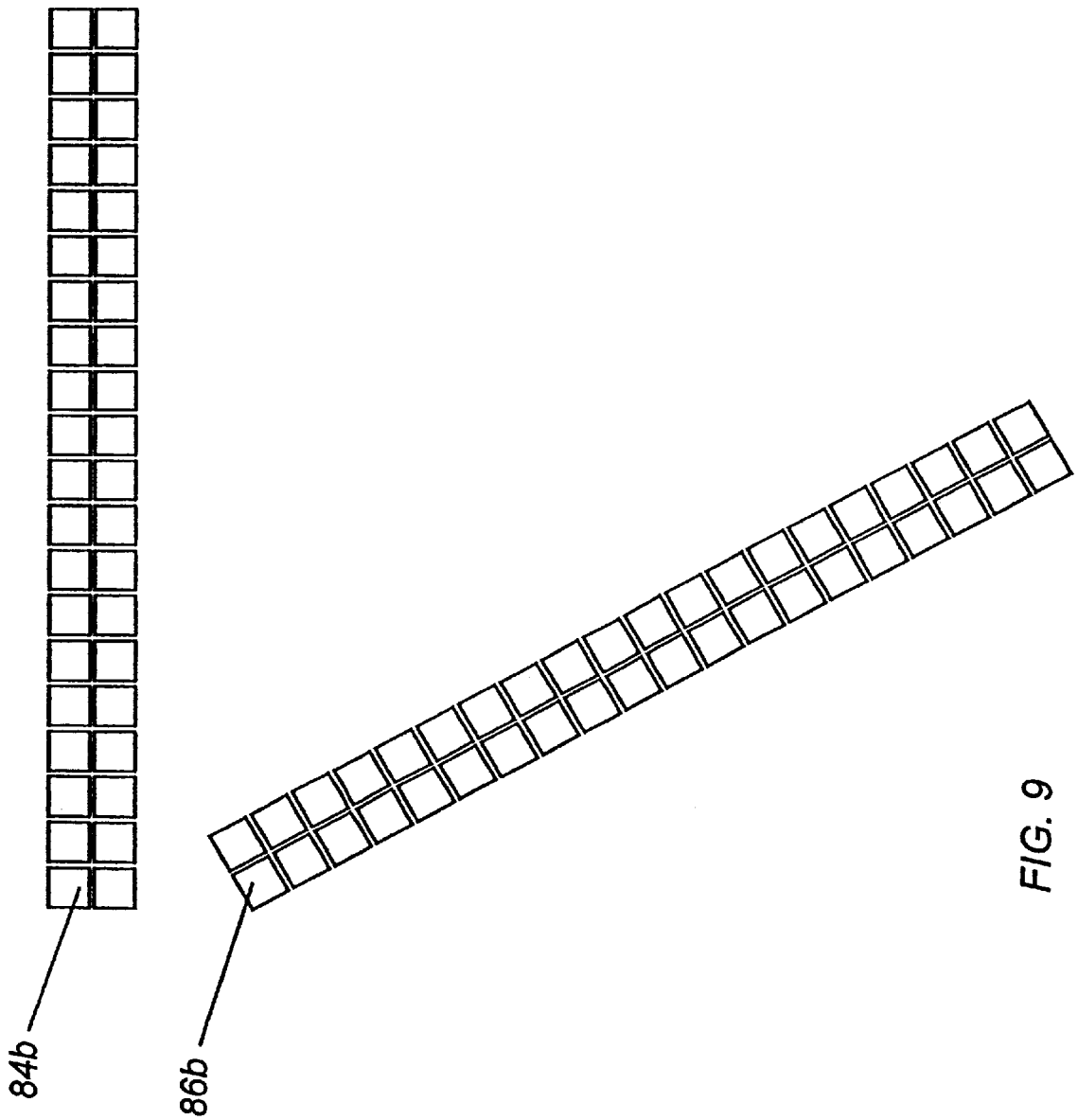
FIG. 9 illustrates the results of rotational accuracy tests which were made using an integrated positioning apparatus, in accordance with an embodiment of the invention.

The high degree of accuracy provided by the positioning device was demonstrated in accuracy tests which quantitatively and qualitatively measure the radiation dose delivered to a phantom (e.g., a piece of x-ray film) under a variety of conditions. FIGS. 6 and 8 depict the results of x, y positional and rotational accuracy tests, respectively, which were performed using a prior art device. FIGS. 7 and 9 depict the results of identical accuracy tests, respectively, which were performed using an embodiment of an integrated positioning device. The purposes of the tests were to quantify and compare the abilities of the two devices to accurately position the tabletop, and ultimately, the patient. Three separate tests were conceived and run. The first two tests are depicted in FIGS. 6 and 7. Two identical reference grids 74a and 74b are shown in FIGS. 6 and 7. These grids are used as a reference to determine the accuracy of the test patterns of the second and third tests as described below.

The first test involves match-line strip) patterns 76a and 76b as shown in FIGS. 6 and 7 respectively. As described previously, a tomotherapy delivery scheme treats one thin slice of the tumor at a time. The longer the tumor, the more slices there are to be treated. The region where the radiation slices meet is known as the match-line. Clearly the match-line must be positioned perfectly, so that the adjacent strips of radiation do not overlap, creating a "hot" strip due to double closing of the region. Likewise, if the match-line line were created such that the two radiation strips did not touch, then there would result a "cold," or under dosed, region that was not treated at all. The importance of the match-line, and its sensitivity to hot and cold regions, make it a perfect test of a tabletop positioning device. The idea behind the test was to deliver multiple 2 cm by 20 cm strips of radiation adjacent to each other. The radiation fields would be delivered to x-ray film, which would darken due to the exposure. The exact spacing of the fields necessary to produce a perfect match-line is known. Theoretically, it should be possible to build a large field of darkening on the film with no evidence that the large field was actually comprised of many adjacent small fields. The adjacent fields of radiation are positioned by taping an x-ray film to the tabletop, and moving the tabletop using the tabletop positioning device. The film just described is often referred to as a match-line film, and is actually employed during the acceptance testing and commissioning of a clinical tomotherapy treatment system. The test exploits the high resolving capability of x-ray film, which is capable of resolving as many as 100 line pairs per millimeter.

Comparing the prior art device match line pattern 76a in FIG. 6 with the integrated positioning device's match line pattern 76b in FIG. 7 reveals several limitations of the prior art device. As seen in FIG. 6, several overlaps 80 or "hot spots" of radiation treatment are visible. Additionally, a gap 82 or "cold spot" of radiation is also visible. Each of these conditions is a direct result of inaccurate alignment of the tabletop by the prior art positioning device. In contrast, the match line pattern 76 in FIG. 7 of the integrated positioning device is free of these defects.

The second test was conducted by applying a grid of pencil beams to an x-ray film so as to produce a very specific pattern of darkening (due to x-ray exposure) on the film. As in the previous test, the deviation of the pattern from an "ideal" pattern would serve to quantify the positional accuracy of the system. The difference from the first test is that the second test quantifies accuracy in both the longitudinal direction (as did test the first test) and the lateral, or x, direction. The multi-leaf collimator delivers a 2 cm long by 20 cm wide field of radiation when all 40 of its pencil beams are opened. The steps of the second test are: 1.) open alternating pencil beams of radiation in a checkerboard fashion in order to deliver one half of the full field of radiation; 2.) move the x-ray film to a new x, y location by shifting the table in the x and y directions using the positioning device; 3.) return to the original x, y location of step 1 by shifting the positioning tables back to the original position's x, y coordinates; and 4.) open the opposite pencil beams to deliver the remaining one half of the full field. If the table has been accurately returned to the exact same position as in step 1, the x-ray pattern will look exactly like a full field reference pattern 74a and 74b that was delivered in the same method involving two "halves" without table movement.

Upon examination, various overlaps and gaps can be seen in the displacement test grid 78a as compared with the reference grid 74a in FIG. 6. These defects are due to inaccurate re-alignment of the tabletop. In comparison, FIG. 7 shows the displacement test grid 78b made with the integrated positioning device is identical to the initial reference grid 74b.

The third and final test was conceived to quantify the errors introduced when x, y displacement of the couch was combined with couch rotation. As was described previously, research has shown that patient treatments can often be improved significantly by approaching the tumor from multiple directions by rotating the couch to a new angle. The third test was performed identically to the second test, with the exception that, in addition to the x, y translation, the couch was also rotated to a new couch angle. This test served to introduce the potential for additional errors due to the previously discussed process of dragging and or pushing a freestanding positioning device beside the couch. In FIG. 8, the prior art device can be seen to have introduced significant errors in the rotational test grids 84a and 86a. In comparison, FIG. 9 shows the integrated positioning device produced virtually identical rotational test grids 84b and 86b. These results are the same as the second test where no couch rotation was employed. The tests demonstrate that the integrated positioning de ice's positional accuracy is unaffected by couch rotation, while the prior art device introduces extremely large, and possibly disastrous errors.

In use, the table top positioning device is particularly suitable for IMRT at multiple couch angles. The results of the previously described tests demonstrate that treatment of a tumor at multiple couch angles, while using the positioning device, can be accomplished at a degree of accuracy sufficient to avoid any "hot" or "cold" spots. The tabletop positioning device positions and locks the tabletop of the couch in the lateral and longitudinal positions to an accuracy of 0.01 mm. As the couch is rotated to a different treatment angle, the positioning device rotates with the couch as an integral part of the device. Consequently, the tabletop maintains its positioning accuracy relative to the established isocenter.

In an alternative embodiment, the movement of the positioning tables is powered by electronically controlled motors which are mounted on the side of each table. The motorized embodiment uses 1 micron resolution linear encoders for a feedback position loop. The command to change position may be sent electronically from the IMRT controlling computer using the treatment software. Other types of mount techniques and positioning indicators may also be used.

The present embodiment of the integrated positioning device weighs approximately 65 lbs (the motorized version weighs approximately 50 lbs.). It can be. mounted on the treatment couch by hand. Alternatively, the positioner may be placed on a wheeled cart and rolled up and docked on the side of the couch. In either case, the device is preferably designed to be detachable for easy removal. This allows the integrated positioning device to be space efficient, which is often a concern in a small treatment vault.

In addition to enabling treatment at multiple couch angles, the degree of accuracy offered by the integrated positioning device provides for alternative methods of use in radiation therapy. These methods include cerebral spinal axis (CSA) treatment, breast cancer treatment, matching adjacent electron fields, etc. The longitudinal movement of the couch and patient for tomotherapy treatments is quite simply an exercise in "matching" abutting fields. As in IMRT, the goal is to relocate the patient so that a second delivered field will align perfectly with the edge of the previously defined field. An extremely accurate alignment is necessary to avoid the previously described hot and cold spots at the match line. In non-IMRT, conventional treatments there is frequently a need to "match" two or more fields. For example, in breast cancer treatment, there is a need for five field breast matching of super claviacular fields to parallel opposed tangential breast fields. In CSA, treatments occur with multiple fields along virtually the entire length of the spinal cord. An inaccurate match line resulting in a hotspot on the spinal cord can result in paralysis of a patient due to a radiation induced transection of the cord. Additionally, if a tumor can be treated without the movement of the patient to different couch angles, the positioning device can be used to provide an extremely accurate positioning of the treatment tabletop Another alternative use is for validation of treatment plans and commissioning a new device with the accurate positioning of a dose measurement device (e.g., water tank, film, ionization device).

The advantages of the disclosed invention may include an integrated positioning device that is mounted on the treatment couch. Another advantage is the capability of the device to position and lock the tabletop of the couch in the lateral and longitudinal positions to an accuracy of less than 0.01 mm. When the treatment couch is rotated to a different couch angle, the integrated positioning device rotates as an integral part of the couch and as a result, it maintains the positioning accuracy of the tabletop relative to the isocenter of the patient.

While the invention has been disclosed with reference to specific examples of embodiments, numerous variations and modifications are possible. Therefore, it is intended that the invention not be limited by the description in the specification, but rather the claims that follow.

What is claimed is:

1. An apparatus for positioning a moveable tabletop on a treatment couch comprising:
   a central frame which is adapted to be mounted on an exterior of the treatment couch;
   a connecting mechanism adapted to be coupled to the moveable tabletop, wherein the connecting mechanism is coupled to the central frame; and
   a positioning mechanism on the central frame which is adapted to position the moveable tabletop to a desired location in lateral and longitudinal directions.

2. The apparatus of claim 1, wherein the central frame is detachably mounted on the treatment couch.

3. The apparatus of claim 1, wherein the connecting mechanism is removably coupled to the moveable tabletop.

4. The apparatus of claim 1, wherein the positioning mechanism comprises:
   a lateral positioning table which positions the moveable tabletop to a desired location in the lateral direction; and
   a longitudinal positioning table which positions the moveable tabletop to a desired location in the longitudinal direction.

5. The apparatus of claim 4, wherein the positioning mechanism further comprises:
   a motor for the lateral positioning table; and
   a motor for the longitudinal positioning table.

6. The apparatus of claim 1, wherein the positioning mechanism comprises a locking mechanism adapted to lock the moveable tabletop in the desired location in the lateral and longitudinal directions.

7. The apparatus of claim 1, wherein the positioning mechanism positions the moveable tabletop in a lateral direction to within 0.01 millimeters.

8. The apparatus of claim 1, wherein the positioning mechanism positions the moveable tabletop in a longitudinal direction to within 0.01 millimeters.

9. A method for positioning a moveable tabletop on a treatment couch to receive radiation treatment comprising:
   mounting a central frame on an exterior of the treatment couch;
   coupling at least one connecting mechanism to the moveable tabletop, wherein the connecting mechanism is coupled to the central frame; and
   positioning the moveable tabletop to a desired location in lateral and longitudinal directions with a positioning mechanism on the central frame.

10. The method of claim 9, wherein the central frame is detachably mounted on the treatment couch.

11. The method of claim 9, wherein the connecting mechanism is removably coupled to the moveable tabletop.

12. The method of claim 9, wherein the moveable tabletop is positioned to the desired location in the lateral direction by a first positioning table and the moveable tabletop is positioned to the desired location in the longitudinal direction by a second positioning table.

13. The method of claim 12, wherein the first and second positioning tables are positioned to the desired locations in the lateral and longitudinal directions by a motor.

14. The method of claim 9 further comprising:
   locking the moveable tabletop in the desired location in the lateral and longitudinal directions.

15. The method of claim 9 further comprising:
   applying a radiation treatment from a radiation treatment device;
   rotating the treatment couch to a different angle relative to the radiation treatment device; and
   positioning the moveable tabletop to a second desired location in the lateral and longitudinal directions.

16. The method of claim 9, wherein the moveable tabletop on a treatment couch is positioned to receive breast cancer treatment.

17. The method of claim 9, wherein the moveable tabletop on a treatment couch is positioned to receive cerebral spinal axis treatment.

18. The method of claim 9, wherein the moveable tabletop on a treatment couch is positioned to commission a radiation treatment device.

19. The method of claim 9, wherein the moveable tabletop on a treatment couch is positioned to validate a radiation treatment plain.

20. An apparatus for positioning a moveable tabletop on a treatment couch comprising:
   means for mounting a central frame on an exterior of a base of the treatment couch;
   means for connecting the central frame to the moveable tabletop;
   means for positioning the moveable tabletop to a desired location in a lateral direction; and
   means for positioning the moveable tabletop to a desired location in a longitudinal direction.

21. An apparatus for positioning a moveable tabletop on a treatment couch comprising:
   a central frame for mounting on an exterior of the treatment couch;
   a first connecting mechanism coupled to the central frame and attachable to the treatment couch;

a second connecting mechanism coupled to the central frame and attachable to the moveable tabletop; and a positioning mechanism on the central frame to position the moveable tabletop to a desired location in lateral and longitudinal directions.

22. The apparatus of claim 21, wherein the central frame is detachably mounted on the treatment couch.

23. The apparatus of claim 21, wherein the first connecting mechanism is removably attached to the treatment couch.

24. The apparatus of claim 21, wherein the second connecting mechanism is removably attached to the moveable tabletop.

25. The apparatus of claim 21, wherein the positioning mechanism comprises:

a lateral positioning table which positions the moveable tabletop to a desired location in the lateral direction; and a longitudinal positioning table which positions the moveable tabletop to a desired location in the longitudinal direction.

26. The apparatus of claim 25, wherein the positioning mechanism further comprises:

a motor for the lateral positioning table; and a motor for the longitudinal positioning table.

27. The apparatus of claim 21, wherein the positioning mechanism comprises a locking mechanism adapted to lock the moveable tabletop in the desired location in the lateral and longitudinal directions.

28. The apparatus of claim 21, wherein the positioning mechanism positions the moveable tabletop in a lateral direction to within 0.01 millimeters.

29. The apparatus of claim 21, wherein the positioning mechanism positions the moveable tabletop in a longitudinal direction to within 0.01 millimeters.

30. A method for positioning a moveable tabletop on a treatment couch to receive radiation treatment comprising:

mounting a central frame on an exterior of the treatment couch with a first connecting mechanism;

coupling the central frame to the moveable tabletop with a second connecting mechanism; and positioning the moveable tabletop to a desired location in lateral and longitudinal directions with a positioning mechanism on the central frame.

31. The method of claim 30, wherein the central frame is detachably mounted on the treatment couch.

32. The method of claim 30, wherein the first connecting mechanism is removably attached to the treatment couch.

33. The method of claim 30, wherein the second connecting mechanism is removably attached to the moveable tabletop.

34. The method of claim 30, wherein the moveable tabletop is positioned to the desired location in the lateral direction by a first positioning table and the moveable tabletop is positioned to the desired location in the longitudinal direction by a second positioning table.

35. The method of claim 34, wherein the first and second positioning tables are positioned to the desired locations in the lateral and longitudinal directions by a motor.

36. The method of claim 30, further comprising:

locking the moveable tabletop in the desired location in the lateral and longitudinal directions.

37. The method of claim 30, further comprising:

applying a radiation treatment from a treatment device;

rotating the treatment couch to a different angle relative to the treatment device; and positioning the moveable tabletop to a second desired location in the lateral and longitudinal directions.

* * * * *

UNITED STATES PATENT AND TRADEMARK OFFICE
CERTIFICATE OF CORRECTION

PATENT NO. : 6,634,790 B1
DATED : October 21, 2003
INVENTOR(S) : Bill J. Salter, Jr.

It is certified that error appears in the above-identified patent and that said Letters Patent is hereby corrected as shown below:

Column 2,
Line 37, the word "alms" is corrected to read -- arms --.

Signed and Sealed this

Twentieth Day of April, 2004

JON W. DUDAS
*Acting Director of the United States Patent and Trademark Office*